United States Patent [19]

Huang et al.

[11] Patent Number: 5,089,205
[45] Date of Patent: Feb. 18, 1992

[54] PROCESS FOR PRODUCING MEDICAL DEVICES HAVING ANTIMICROBIAL PROPERTIES

[75] Inventors: Wu-Nan Huang, Greer; Niles R. Manwill, Belton; Fung-Bor Chen, Greer, all of S.C.

[73] Assignee: Becton, Dickinson and Company, Franklin Lakes, N.J.

[21] Appl. No.: 411,939

[22] Filed: Sep. 25, 1989

[51] Int. Cl.$^5$ .................... B29C 41/02; B29C 41/22
[52] U.S. Cl. ........................ 264/255; 2/168; 264/305; 264/308; 264/DIG. 30; 264/334; 424/404; 424/485; 427/413; 427/2
[58] Field of Search ............... 2/167, 168; 264/300, 264/305, 308, 255, DIG. 30, 306, 307, 334; 424/404, 485; 427/157, 413, 2; 156/242; 604/292; 425/2, 275

[56]     References Cited
         U.S. PATENT DOCUMENTS

| | | | |
|---|---|---|---|
| 2,951,766 | 9/1960 | White | 106/18.31 |
| 3,347,233 | 10/1967 | Migliarese | 604/292 |
| 3,384,083 | 5/1968 | Cozza et al. | 604/292 |
| 3,566,874 | 3/1971 | Shepherd | 604/265 |
| 3,579,628 | 5/1971 | Gander et al. | 424/445 |
| 3,662,054 | 5/1972 | Wollmann et al. | 264/300 |
| 3,695,921 | 10/1972 | Shepherd et al. | 427/2 |
| 3,896,807 | 7/1975 | Buchalter | 604/289 |
| 3,945,049 | 3/1976 | Barlow | 2/167 |
| 4,143,109 | 3/1979 | Stockum | 264/308 |
| 4,283,244 | 8/1981 | Hashmi | 156/242 |
| 4,381,380 | 4/1983 | LeVeen et al. | 525/452 |
| 4,479,795 | 10/1984 | Mustacich et al. | 604/53 |
| 4,521,564 | 6/1985 | Solomon et al. | 525/54.1 |
| 4,642,242 | 2/1987 | Solomon et al. | 427/2 |
| 4,675,347 | 6/1987 | Mochizuki et al. | 523/122 |
| 4,678,660 | 7/1987 | McGary et al. | 424/25 |
| 4,713,402 | 12/1987 | Solomon | 523/112 |
| 4,853,978 | 8/1989 | Stockum | 2/167 |
| 4,884,990 | 12/1989 | Lovik | 427/157 |

FOREIGN PATENT DOCUMENTS

| | | |
|---|---|---|
| 0229862 | 7/1987 | European Pat. Off. . |
| 60-36064 | 2/1985 | Japan . |
| WO86/02561 | 5/1986 | PCT Int'l Appl. . |
| 2084466 | 4/1982 | United Kingdom . |

OTHER PUBLICATIONS

"An experimental Histopathologic Study of Surgical Glove Powders" Arch Surg-vol. 119, Feb. 1984, pp. 215-219.

*Primary Examiner*—Jeffery Thurlow
*Assistant Examiner*—Mathieu Vargot
*Attorney, Agent, or Firm*—Robert P. Grindle; Arthur D. Dawson

[57]     ABSTRACT

A process for imparting enhanced antimicrobial properties to medical devices, and particularly surgical and examination gloves, and to such gloves produced by the process. The process involves partially forming the gloves by dipping glove molds into a latex composition, for example, and prior to curing or heating to final form, dipping the already coated forms into a second composition containing an antimicrobial agent, and thereafter curing or heat setting the finally produced glove prior to stripping from the form. Alternatively, the antimicrobial composition can be additionally or independently applied to a cured glove before stripping. The result is a glove which prevents, or decreases the potential of, cross-contamination between the glove users and patients because it will kill or reduce the susceptible microorganisms prior to or after penetration of the basic material forming the glove.

8 Claims, No Drawings

PROCESS FOR PRODUCING MEDICAL DEVICES HAVING ANTIMICROBIAL PROPERTIES

BACKGROUND AND STATEMENT OF THE INVENTION

This invention relates to a process for producing medical devices on dipping forms, such as surgical and examination gloves or condoms, for example. More particularly, this invention is directed to such a process which imparts superior antimicrobial properties to such devices without causing toxic reactions to the user.

In processes for producing antimicrobial devices it has been routine to incorporate the antimicrobial agent into the material that forms the device, either by including the antimicrobial agent in the device material prior to fabrication or by treatment of the fabricated and functionally independent devices with an antimicrobial agent. Also, when integrating a cationic antimicrobial agent into an anionic latex there are problems of ionic incompatibility. U.S. Pat. No. 4,675,347 describes a technique to resolve the problem by changing the ionic nature of the latex from anionic to cationic or non-ionic through emulsification of the latex with a cationic or non-ionic surfactant.

The special feature of this invention is that by first partially forming flexible gloves in a procedure wherein an initial dipping takes place for forming a latex glove, for example, and subsequently dipping the already formed latex layer into a second bath or dispersion which contains the antimicrobial material, superior antimicrobial results are obtained from the objects produced by such a procedure. That is, when the gloves or other objects of interest formed here, are stripped from the form, the internal surface has the antimicrobial properties immediately adjacent to the wearer's skin when the gloves are subsequently donned by a surgeon, or clinical staff personnel for examination purposes.

Another special feature of this invention is that a cationic antimicrobial agent can be neutralized by the addition of a nonionic or anionic surfactant to overcome the problem of incompatibility of the cationic antimicrobial agent with the anionic latex during mixing.

Many attempts to solve the problem of infection have been directed toward incorporating into plastic articles such as catheters and vascular grafts an antimicrobial agent. For example, U.S. Pat. No. 3,695,921 discloses a catheter coated with a layer of hydrophilic polymer having an antibiotic absorbed therein. European published Application No. 229,862 teaches thermoplastic polyurethane medical devices having an antimicrobial agent on its surface. In addition, U.S. Pat. No. 4,581,028 teaches infection resistant plastic medical articles, such as vascular grafts, having incorporated antimicrobial agents such as silver sulfadiazine and pipericillin. These articles are prepared by dipping procedures.

In addition, U.S. Pat. No. 4,479,795 discloses medical devices of permeable polymers, including a carboxylate antimicrobial agent, which diffuses to the surface of the device to form an antimicrobial barrier. Japanese Patent Application No. SHO 60-36064 teaches a polyurethane or silicone catheter dipped in an aqueous solution of chlorhexidine to absorb the chlorhexidine into the polymer. PCT Published Application No. W086/02561 teaches a medical device of a hydrophobic thermoplastic polymer having up to one percent chlorhexidine base coated thereon or incorporated therein.

Other publications along this line include U.K. Patent Application No. 2084466A, U.S. Pat. No(s). 4,713,402, 4,521,564 and 4,642,242.

Finally, U.S. Pat. No. 4,678,660 discloses a polyurethane article having coated on the surface thereof a layer of polyurethane alloy containing a dispersed complex of a guaternary salt with either an antithrombogenic agent or an antibiotic agent.

In each case, with the prior art discussed above, the antimicrobial agent is incorporated into the material as opposed to being incorporated into a layer applied to an already formed layer of the article still present on the dipping form.

In considering generally the conditions for carrying out the invention herein, one may note that an antimicrobial glove may be made by coating or treating the glove with a material containing the antimicrobial agents. Bisbiguanides have long been used for this purpose and chlorhexidine is the best known product. It has been used for many years in formulations for hand washes and surgical scrubs. However, the material, as stated above, was applied in the dispersions or other formulations forming the device, or absorbed into the surface. No one has suggested incorporating the antimicrobial agent into a separate dispersion or composition for a separate application to an already partially formed layer of the object in question. Also no one has proposed the use of an anionic latex directly with a modified cationic antimicrobial agent.

For example, a gelled latex glove film in accordance with this invention may be dipped into a polyurethane aqueous dispersion (or solution) or a second latex compound containing P-chloro-m-xylenol, preferably with the dry weight concentration range of within the range of between about five and thirty percent, prior to the normal glove cure process. After curing, the glove is dipped into a lubricant dispersion or solution containing an antimicrobial surfactant such as, for example, Nonidet P-40 which is octylphenoxy-poly(ethoxyethanol) and a chlorhexidine base or its salts such as, for example, acetate, gluconate or hydrochloride, or a combination of these. The preferred range of the chlorhexidine base or its salts and the surfactant is within the range of between about one and fifty percent, and preferably one and ten percent. The glove is then dried and stripped off the glove form.

Alternatively, a gelled latex glove film may be dipped in an aqueous or alcohol lubricant dispersion or solution containing an antimicrobial surfactant such as Nonidet P-40, as discussed above, and a chlorhexidine base or its salts as discussed above. The preferred range of the chlorhexidine base or its salts and the surfactant is within the range of between about one and fifty percent, and preferably one and ten percent. The glove is then dried, cured and stripped off the form.

As a further alternative approach, a regular finished glove may be immersed in an alcohol solution (for example, methanol, ethanol or isopropanol) or an aqueous solution containing an antimicrobial surfactant such as Nonidet P-40, as discussed above, and a chlorhexidine base or its salts. The preferred range of the chlorhexidine base or its salts and the surfactant is within the range of between about one and fifty percent, and preferably one and ten percent.

As further representative of a general procedure for use in the invention here, a non-latex glove such as plasticized polyvinyl chloride is coated with a solvent based solution consisting of flexible polymers such as, for example, soft polyurethane in methylene chloride. After the coating is dried, it is dipped in an alcohol or aqueous solution containing an antimicrobial surfactant such as Nonidet P-40 and chlorhexidine base or its salts. In this case, the preferred range, again, of the chlorhexidine base or its salts and the surfactant is within the range of one and fifty percent and preferably one and ten percent. The glove is then dried in the final step required prior to stripping, and then stripped off the form.

Alternatively, while the fused plasticized PVC glove is still on the form, it can be dipped into dispersion A described in Example I below, preferably with a higher wetting capability.

The invention here is particularly useful in providing elimination of a wide spectrum of microorganisms. organisms. For example, the layer containing P-chloro-m-xylenol provides a means for killing microorganisms when they try to penetrate the inner layer of glove material. The octylphenoxy- poly (ethoxyethanol) has proven effective against HIV virus, while the addition of chlorhexidine provides either a synergistic or additional effect against microorganisms.

It will be appreciated that with the method of the invention here, the laminates produced may be utilized in various configurations for wear, as discussed above, such as, for example, surgeon's gloves, examination gloves and condoms.

As further illustrative of the method of the invention here, one may note the following examples in which materials are prepared in accordance with the invention here and subsequently tested for their antimicrobial properties. It is to be understood, however, that these examples are being presented with the understanding that they are to have no limiting character on the broad disclosure of the invention, as generally set forth herein, and as directed to one skilled in the art.

EXAMPLE I

Chlorhexidine diacetate was added to an aqueous dispersion used in lubricating the inside surface of a surgical glove (the side against the surgeon's hand). The new modified lubricant dispersion had the following composition:

| Dispersion A | |
| --- | --- |
| Component | Percent by dry weight |
| A Starch powder, USP | 14 |
| B Silicone | 1 |
| C Polyethylene glycol p-isooctylphenyl ether | 0.04 |
| D Chlorhexidine Diacetate | 0.3 |
| E Dimethoxane | 0.08 |
| F Methyl Cellulose | 0.08 |

The lubricant dispersion had a solids content of fifteen percent, and the chlorhexidine diacetate was added at a concentration of two percent of the total dry solids content of the dispersion.

Dispersion A was applied to the glove surface by dipping a glove form having a gelled and washed natural latex film into Dispersion A, before passing the glove into the curing oven. Then, the glove was passed through the oven which caused Dispersion A to dry into a coated powder form. After the oven cure, the glove was inverted during stripping, placing it in its final form with the dried Dispersion A powder on the glove's interior surface.

The antimicrobial efficacy of the glove surface containing the dried Dispersion A powder was evaluated by determining the existence and zone diameter of inhibited bacterial growth caused by placing the test sample over a nutrient agar surface inoculated with a soil of Staphylococcus Aureus. The sample was prepared by cutting a 6 mm diameter disc from the antimicrobial treated glove. The disc was applied, treated side down, to the inoculated agar surface for a period of 60 minutes at ambient conditions, and then removed. The agar plate was placed in a 37° C. incubator overnight. After incubation, the agar plate was found to have an 11 mm zone of bacterial inhibition at the point of sample contact.

In order to acquire information on the rate of bacterial inhibition, six (6) 6 mm diameter discs were cut from the glove sample and applied, antimicrobial treated side down, on a nutrient agar surface inoculated with a soil of Staphylococcus Aureus for different lengths of time and then removed. The contact exposure times used were 1, 5, 10, 15, 30 and 60 minutes. At the completion of sample exposure, each agar plate was incubated at 37° C. overnight. Then the diameters of zones of bacterial inhibition, if any, were measured. The same tests were repeated on the antimicrobial glove samples aged at 70° C. for one week. The results are as follows:

| Exposure Time (Minutes) | No Accelerated Aging Applied to Samples | Samples with Accelerated Aging, @ 70° C. for One Week |
| --- | --- | --- |
| | Zone of Inhibition (mm) | |
| 1 | 8.0 | 7.3 |
| 5 | 8.0 | 7.3 |
| 10 | 8.7 | 8.0 |
| 15 | 8.3 | 8.7 |
| 30 | 9.7 | 8.3 |
| 60 | 11.0 | 10.7 |

As can be seen, there is clear inhibition, immediately, and over time, whether room temperature or accelerated aging.

A primary skin irritation test was performed on the samples. Six adult female New Zealand albino rabbits were used. Prior to application of the samples, the rabbits' backs were clipped free of hair. Two sites were chosen on each rabbit, with skin left intact on one, and abraded on the other. The samples were applied to an area of skin approximately one inch square at each site. Patches of surgical gauze measuring one inch square, two single layers thick, were applied over the samples, and covered with a non-reactive tape. The rabbits were then wrapped with a binder. The binders and the tape were removed after 24 hours. An evaluation of the skin reaction was made at 24 and 72 hours after application of the samples. The rabbits showed no signs of edema or erythema demonstrating that the sample was non-irritating (Primary Irritation Index = 0.00).

Control—Example I

Ten 6 mm sample discs were cut from a love prepared with a lubricating dispersion in the same manner and with the same content as above, but not containing chlorhexidine diacetate. The samples were placed, lubricant side down, onto nutrient agar plates inoculated with a soil of Staphylococcus Aureus and remained in contact with the agar surface for 60 minutes before removal. The agar plates were placed into a 37° C. incubator overnight. After incubation, all of the agar plates were observed to have no zones of bacterial inhibition, clearly indicating no antimicrobial activity.

EXAMPLE II

An aqueous emulsion was prepared by mixing an acrylic polymer emulsion (for example, Rhoplex HG-74) and a chlorhexidine gluconate solution. The aqueous emulsion had the following composition:

| Component | Percent by dry weight |
|---|---|
| A Rhoplex HG-74 | 2 |
| B Chlorhexidine gluconate | 0.4 |

The dry weight ratio of acrylic polymer to chlorhexidine gluconate was 5:1. The total solid contents of the mixed emulsion was about two percent. This dispersion was used to apply a coating over an already formed natural rubber latex gel film on conventional ceramic forms used in a glove production line. After drying and curing, the hot forms were lubricated by dipping in an aqueous powder dispersion, followed by drying in open air. The formed loves were then inversely stripped, placing the polymer coated side as the inside surface of the glove.

The same test procedures for the determination of rate of bacterial inhibition as shown in Example I were used to obtain the antimicrobial efficacy of the samples. The results are as follows:

| Exposure Time (Minutes) | Zone of Inhibition (mm) |
|---|---|
| 1 | 7.3 |
| 5 | 8.7 |
| 10 | 8.7 |
| 15 | 9.0 |
| 30 | 9.7 |
| 60 | 11.0 |

As in Example I, there is clear indication of inhibition, immediately, and over time.

A primary skin irritation test (same procedure as shown in Example I) was performed on the samples. None of the rabbits showed any signs of erythema or edema, clearly indicating that the sample was non-irritating (Primary Irritating Index = 0.00).

A human tissue cell cytotoxicity titre was also performed on the samples. Three (3) two fold dilutions were required before the cell culture would survive exposure to the samples. This indicated a cytotoxicity titre 8 which is comparable to most of the commercially available surgeon's gloves.

EXAMPLE III

A polymer coating dispersion was prepared by adding P-chloro-m-xylenol to a twenty percent aqueous dispersion of polyester-polyurethane (Impranil DLN manufactured by Mobay). The polymer coating dispersion had the following composition:

| Component | Dispersion Percent by dry weight |
|---|---|
| A Impranil DLN | 20 |
| B P-chloro-m-xylenol | 2 |

The P-chloro-m-xylenol (PCMX) was added at a concentration of ten percent of the dry polymer weight in the dispersion. The coating solution was used in a glove making process so that a love form, already possessing a natural rubber latex gel on its surface, could be dipped into the coating dispersion before entering the curing ovens. Once cured, the glove was dipped into a lubricant dispersion containing five percent chlorhexidine diacetate of the total dry weight.

The glove sample was tested for antimicrobial efficacy by placing a 6 mm disc cut from the sample, coating side down, on the surface of a nutrient agar plate inoculated with a soil of Staphylococcus Aureus and incubating the plate overnight at 37° C. After incubation, the diameter of the zone of microbial inhibition across the center of the sample was measured. The sample disc showed a 15.3 mm zone of inhibition around the sample disc. The incorporation of P-chloro-m-xylenol is to kill the PCMX destructible microorganisms during the migration, diffusion or penetration of the microorganisms through the polyurethane coating. Thus, the outer latex coating is maintained free of such migration or diffusion.

EXAMPLE IV

The finger portion was cut from a TRUE TOUCH ® vinyl exam glove and slipped over a ceramic finger cot form. TRUE TOUCH ® is a trademark of Becton, Dickinson and Company, Franklin Lakes, New Jersey. The sample was then dipped into a polymer solution (five percent of Becton Dickinson Polymer Research soft thermosetting polyurethane, lot #8735-37, in $CH_2Cl_2$) and dried at 105° C. for 5 minutes. The finger sample was then dipped into an aqueous lubricant dispersion. The dispersion had the following composition:

| Component | Dispersion Percent by dry weight |
|---|---|
| A Chlorhexidine digluconate | 1.8 |
| B Starch powder, USP | 12.7 |
| C Silicone | 0.91 |
| D Polyethylene glycol p-iso-octylphenyl ether | 0.03 |
| E Dimethoxane | 0.08 |
| F Methyl cellulose | 0.08 |

The dispersion contained about twelve percent (wt./wt.) chlorhexidine digluconate in total dry powder, dried at room temperature, and stripped from the form in the usual manner so that the outer surface on the form became the inner surface of the glove in use. The sample was then tested for antimicrobial efficacy by determining the zone of bacterial inhibition around a sample disc as described by the method used in Example III. The sample produced a zone of inhibition vs. Staphylococcus Aureus of 10.3 mm.

EXAMPLE V

A solution was prepared by first dissolving one part (wt.) chlorhexidine digluconate (CHG) into three parts of an anionic surfactant such as DowFax 2EP. Then the CHG/surfactant solution was added to a twenty percent polyurethane dispersion (for example Impranil DLN manufactured by Mobay) to obtain a dispersion consisting of 1:5 wt. ratio of dry CHG/surfactant to dry polyurethane. The dispersion had the following composition:

| Dispersion | |
|---|---|
| Component | Percent by dry weight |
| A Impranil DLN | 20 |
| B Chlorhexidine digluconate | 1 |
| C DowFax 2EP | 3 |

The Impranil DLN dispersion is anionic and chlorhexidine digluconate is cationic. Therefore, the latter had to be converted to an anionic or nonionic solution by mixing it with an anionic or nonionic surfactant to eliminate the CHG cationic nature prior to the addition of CHG solution to the anionic polyurethane dispersion. The coating dispersion was used to prepare gloves as follows:

Glove forms containing already formed gelled natural rubber film on their surfaces were dipped into the dispersion to form a coating over the latex layer, and then the composite glove film was cured. Once cured, the glove film was dipped into the lubricant dispersion A as described in Example I, but without chlorhexidine diacetate, followed by open air drying to bring the gloves to final form for stripping, and then the gloves were inversely stripped from the form.

Using the same procedure as described in Example I for the measurement of the rate of bacteria inhibition, we obtained the following results:

| Exposure Time (Minutes) | Zone of Inhibition (mm) |
|---|---|
| 1 | 2.0 |
| 5 | no zone |
| 10 | 5.0 |
| 15 | 3.3 |
| 30 | 7.0 |
| 60 | 8.0 |

A primary skin irritation test was performed on the sample using the same test procedure shown in Example I. None of the rabbits showed any signs of edema or erythema which demonstrated that the sample was non-irritating (Primary Irritation Index=0.00).

A human tissue cell cytotoxicity titre was also performed on the sample. Three two-fold dilutions were required before the cell culture would survive exposure to the sample extract. The sample has a cytotoxicity titre of 8 which is comparable with most commercially available regular non-antimicrobial treated surgeon's gloves.

While the above examples disclose procedures for making gloves for specific medical applications, it will be appreciated by those skilled in the art that the method of the invention here and the various laminates so produced by the method may be utilized for other applications, including condoms and other medical devices, for example.

While the methods and products herein disclosed form preferred embodiments of the invention, this invention is not limited to those specific methods and the products so produced by those methods, and changes can be made therein without departing from the scope of the invention which is defined by the appended claims. For example, as will be appreciated by practitioners-in-the-art, various different elastomeric coatings may be utilized, selecting a wide variety of polymers in order to have an ultimate final glove with the desired properties. Moreover, the formulations of these compositions may be varied in order to have a thicker or thinner coating, as required for comfort in use, dexterity, sense of feel or protection, as will be appreciated.

What is claimed is:

1. A method for producing a medical device positioned adjacent the skin of the user, with the device having antimicrobial properties, the steps which comprise:
   (a) selecting in a first selecting step gelled anionic natural latex for forming the final outer surface of said device;
   (b) using the material selected in said first selecting step and forming in a first forming step the final outer surface of said device;
   (c) selecting in a second selecting step gelled anionic natural latex for forming the final inner surface of said device to be positioned adjacent the skin of the user;
   (d) incorporating into the material from said second selecting step an antimicrobial agent prepared by neutralizing a cationic antimicrobial agent with an anionic surfactant and solubilizing the neutralized agent with a nonionic surfactant to prevent incompatability of said cationic antimicrobial agent in said gelled anionic natural latex;
   (e) using the material selected and modified in said second selecting and incorporation steps and forming in a second forming step the final inner surface of said device by coating said final outer surface of said device from said first forming step with the material selected from the second selecting step;
   (f) in a third forming step, treating said device obtained by said second forming step to obtain a cured device in final form; and
   (g) stripping said cured device obtained in said third forming step from a forming apparatus.

2. The method of claim 1, in which in a final dipping step, dipping said cured device in an aqueous solution containing octylphenoxy-poly (ethoxyethanol) and a chlorhexidine base or the salts thereof.

3. The method of claim 1, in which said incorporating step is carried out with one of a chlorhexidine base, chlorhexidine salts, or mixtures thereof.

4. A method for producing medical gloves in a sequence of steps in a dipping line, said gloves having antimicrobial properties in the internal surface thereof, the steps which comprise
   (a) dipping in a first dipping step one or more glove forms in a material for forming the final outer surface of said medical gloves being formed;
   (b) said first dipping step forming a film which is the final outer surface of said gloves;
   (c) dipping in a second dipping step the coated gloves formed from said first dipping step, said second dipping step being carried out in a bath of an anionic latex for forming the final inner surface of the medical gloves being formed;

(d) prior to said second dipping step, incorporating a cationic antimicrobial component which has been neutralized with an anionic surfactant in the bath for said second dipping step;

(e) heating said gloves formed in said first and second dipping step to bring said gloves to final form;

(f) in a final dipping step, treating said gloves in final form with a treatment selected from the group consisting of an aqueous lubricant dispersion or an anhydrous alcohol lubricant dispersion; and (g) stripping said formed and treated gloves from the forms on which they were formed.

5. The method of claim 4, in which the material for said first dipping step is gelled anionic natural latex.

6. The method of claim 4 in which the bath for said second dipping step is an aqueous anionic latex of natural rubber or polyurethane.

7. The method of claim 4, in which said antimicrobial agent in said incorporating step is one of a chlorhexidine base, chlorhexidine salts, of mixtures thereof.

8. The method of claim 6 in which a third dipping step is carried out by dipping said gloves formed in said first and second dipping step gloves formed in said first and second dipping step in a bath containing octyl-phenoxy-poly(ethoxyethanol) and a chlorhexidine base or the salts thereof.

* * * * *